United States Patent [19]

Hogan et al.

[11] Patent Number: 5,449,064
[45] Date of Patent: Sep. 12, 1995

[54] ON-LINE INTERFACE AND VALVE FOR CAPILLARY ELECTROPHORESIS SYSTEM

[75] Inventors: Barry L. Hogan, St. Louis, Mo.; Susan M. Lunte, Lawrence, Kans.; John F. Stobaugh, Lawrence, Kans.; Craig E. Lunte, Lawrence, Kans.

[73] Assignee: University of Kansas, Lawrence, Kans.

[21] Appl. No.: 206,210

[22] Filed: Mar. 3, 1994

[51] Int. Cl.$^6$ .............................................. B01D 59/22
[52] U.S. Cl. .............................. 204/180.1; 204/299 R; 204/193
[58] Field of Search ................. 204/180.1, 299 R, 193, 204/180.3

[56] References Cited

U.S. PATENT DOCUMENTS

| | | | |
|---|---|---|---|
| 4,529,230 | 0/1985 | Fatula, Jr. | |
| 4,694,832 | 0/1987 | Ungerstedt | |
| 4,994,165 | 2/1991 | Lee et al. | 204/180.1 |
| 5,073,239 | 12/1991 | Hjerten | 204/299 R |
| 5,110,431 | 5/1992 | Moring | 204/180.1 |
| 5,131,998 | 8/1992 | Jorgenson et al. | 204/299 R |
| 5,302,272 | 4/1994 | Klein | 204/180.1 |

OTHER PUBLICATIONS

O'Shea, Telting-Diaz, Lunte and Lunte *Electroanalysis.* 1992, vol. 4 at pp. 463, 468.

O'Shea, Weber, Bammel, Lunte, Lunte and Smith, *chromatographer,* 1992, vol. 608 at pp. 189–195.

Tellez, Forges, Roussin, and Hernandez, *J. Chromatogr. Biomed. Appl.,* 1992, vol. 581 at pp. 257–266.

Damsma, Westernik, DeVreis, Van den Berg, and Horn, *J. Neurochem.* 1987, vol. 48 at pp. 15–23—15–28.

Church and Justice *Anal. Chem.,* 1987, vol. 59 at pp. 7–12 through 7–16.

Boutelle, Fellows, and Cook, *Anal. Chem.,* 1992, vol. 64 at pp. 1790 through 1794 Caprioli and Lyn, *Proc. Natl. Acad. Sci. U.S.A.,* 1990, at pp. 240–243 (mass spectrometry).

Bushey and Jorgenson, *Anal. Chem.,* 1990, vol. 62 at pp. 978–984.

Tsuda and Zare, *J. Chromatogr.,* 1991, vol. 559 at pp. 103–110.

Bioanalytical Systems CMA/20 Microdialysis Probe Brochure, Bioanalytical Systems, Inc.

Bioanalytical Systems CMA/10 Microdialysis Probe Brochure, Bioanalytical Systems, Inc.

Linhares and Kissinger, "In Vivo Sampling Using Loop Microdialysis Probes Coupled to a Liquid Chromatograph", *J. Chromatography,* 1992 vol. 578, pp. 157–163.

Linhares and Kissinger, "Determination of Endogenous Ions in Intercellular Fluid Using Capillary Ultrafiltration and Microdialysis Probes", *J. Pharmaceutical & Biomedical Analysis,* 1993 vol. 11, No. 11/12, pp. 1121–1127.

Bohs, Linhares and Kissinger, "The UniCell: An Amperometric Flow Cell for On–Line Sensing at uL/min Flow Rates", *Current Separations,* 1994, vol. 13:1, pp. 3–5.

Kissinger and Shoup, "Optimization of LC Apparatus for Determinations in Neurochemistry with an Emphasis on Microdialysis Samples," *J. Neuroscience Methods,* 1990, vol. 34, pp. 3–10.

Hogan, Lunte, Stobaugh and Lunte, "On–Line Coupling of In Vivo Microdialysis Sampling with Capillary Electrophoresis", *Anal. Chem.,* 1994, vol. 66, No. 5, pp. 596–602.

*Primary Examiner*—Richard E. Chilcot, Jr.
*Assistant Examiner*—Max H. Noori
*Attorney, Agent, or Firm*—R. Steven Linne; Ice, Miller, Donadio & Ryan

[57] ABSTRACT

An interface is provided for use with a multiple sample acquisition device and a capillary electrophoresis separation device. The interface includes a body member having a base and an upstanding wall defining a generally hollow interior well. The upstanding wall includes an inlet passageway and an outlet passageway. An inlet guide member has an axially extending guide passageway disposed coaxially with the inlet passageway. An outlet guide member has an axially extending guide passageway disposed coaxially with the outlet passageway. An inlet capillary tube has an outer diameter sized for being received by the axially extending passageway of the inlet guide member, and a fluid passageway through which analyte can flow. The inlet capillary tube also includes a first end disposed exteriorly of the well and a second end disposed within the well. An outlet capillary tube has an outer diameter sized for being received in the axially extending guide passageway of the outlet guide member, and a fluid passageway through which analyte can flow. The outlet capillary tube also includes a first end disposed within the well and a second end disposed exteriorly of the well.

23 Claims, 6 Drawing Sheets

ON-LINE INTERFACE AND VALVE FOR CAPILLARY ELECTROPHORESIS SYSTEM

TECHNICAL FIELD OF THE INVENTION

The present invention relates to analytical chemistry devices, and more particularly to components of an on-line sampling system for use with a capillary electrophoresis separation and detection system.

BACKGROUND OF THE INVENTION

Researchers in the biological sciences are greatly interested in obtaining dynamic chemical information about the processes that occur in living systems. Dynamic chemical information relates to attempts to obtain either continuous, or near-continuous samples from the living organism. By obtaining a large number of closely temporally spaced samples of the material of interest from the living organism, one can better obtain information about the interaction between the living organism and the material of interest over a selected time interval.

The use of continuous sampling can permit the user to better elucidate the pathways and kinetics of absorption of a particular compound of interest, to determine how the compound is transformed within the body, and to determine the rate at which the compound is eliminated from the living organism. This information is often necessary to permit the researcher to fully assess the safety of both pharmaceutical and environmental compounds. For example, one might desire information about the reaction of an analgesic compound in a living organism. To determine this, one could give a known amount of the compound to the organism, and obtain continuous tissue samples (e.g., brain fluid) from the animal. By analyzing the brain fluid samples that were withdrawn at various time intervals after giving the analgesic to the animal, one could obtain a great deal of information about the manner in which the analgesic functioned within the living organism. For example, one could determine the amount of time required by a living organism to absorb the analgesic, and to transfer the analgesic to the site (e.g. the brain) from which the sample was being drawn. Further, one could construct suitable experiments to determine the quantity of analgesic that actually arrived at the site of interest, and also determine whether the particular analgesic is being transformed by the body into break-down products, or other compounds different than the analgesic compound itself.

Also, by continuously obtaining samples, one can also determine the amount of time required to remove the particular analgesic system from the living organism. Knowing the rate of elimination of the analgesic can be especially important for enabling its manufacturer to either adjust the dosage, or alter the drug (such as through micro encapsulation) to enable the drug to achieve a proper liter within the living organism for a proper time period.

When determining pharmacokinetic parameters for a particular compound of interest, or its metabolites, it is often necessary to determine these parameters at specific tissue sites. Other times, it is necessary to determine these parameters in the general system of the living organism. The time scale in which the reactions of interest take place, and in which samples must be removed are typically on the order of minutes to days after the compound is given to the organism.

One goal when performing continuous or semi-continuous sampling is to improve the temporal resolution of the sampling and detection process. Temporal resolution relates to the number of data points that one can obtain over a given time span. Figures for temporal resolution are typically given in units of time span. For example, to say that a particular experiment had a temporal resolution of 1 minute means that a data point was taken (or capable of being taken) each minute. Typically, the factor limiting temporal resolution is the time required to accumulate and collect a sample of a size adequate for the particular detection method being used in conjunction with the sampling. As will be appreciated, a lower sample volume requirement will generally enable a better temporal resolution to be achieved.

A good temporal resolution is especially important when detecting the presence of transient compounds that may remain at a tissue site for only a very short time duration. For example, neuropharmacological investigations, such as investigation into the release of neurotransmitters in response to amphetamine or cocaine, require the acquisition of chemical information from specific brain regions, with temporal resolution of seconds to minutes. Stated another way, because the volume and presence of particular compounds are likely to change so rapidly within such a short time period, a large number of closely temporally spaced data points are necessary to obtain truly meaningful kinetic information.

Current methods for obtaining time interval type, sequential multiple sample chemical information from tissues of living systems have usually involved either a postmortem analysis taken at several time points, or the use of biosensors implanted in vivo. Postmortem analyses typically require the use of a large number of animals, with only a single sample being taken from each animal. The "pseudo continuity" of samples is achieved by taking the samples from the different animals at different points in time. The use of postmortem analyses to construct a temporal plot of chemical events is difficult, and often provides ambiguous results. While several compounds can be determined at each time point (and hence from each sample) each animal can provide data for only a single time point. It is therefore preferable in terms of both the quality of data obtained, and from the standpoint of reducing the number of experimental animals needed, to obtain the entire time course (data set) from one animal, by taking a large number of samples over a span of time from the single animal. Although this can be accomplished through the use of a biosensor, biosensors suffer the drawback of providing less chemical information since they are usually limited to monitoring only a single chemical species.

One other difficulty that inhibits the removal of a large number of samples from an animal over a course of time is the generally small volume of sample available. This is especially true when the living organism is a small laboratory animal, such as a rat.

To overcome the sampling difficulties, many researchers use a microdialysis sampling technique. Microdialysis sampling is accomplished by implanting a microdialysis probe that consists of a small, semi-permeable membrane fiber at the site of interest. This fiber is slowly perfused with a sampling solution. The semipermeable microdialysis membrane allows certain molecules of interest to pass from the animal into the sampling solution. Small molecules in the extra-cellular space can diffuse into the microdialysis membrane fiber, and are swept away by the sampling solution, to be collected for analysis. Microdialysis probes can be implanted in many tissues with minimal discomfort to the experimental animal.

The introduction of microdialysis sampling has provided a technique that can continuously monitor chemical reactions in vivo. By using the appropriate analytical method, several compounds can be determined simultaneously. Therefore, microdialysis can provide both the temporal and chemical information needed to determine the behavior and characteristics of a compound of interest over a relatively long time span. As such, microdialysis can provide the information necessary to permit the researcher to fully elucidate certain biochemical processes.

However, one limitation of microdialysis has been the limited temporal resolution that has been achievable to date. While microdialysis is a continuous sampling technique, it is typically coupled to a separation method that requires discrete samples. For example, with liquid chromatography, a discrete "plug" of a sample containing several compounds is inserted at one time into the upstream end of the liquid chromatography column. As the sample flows downstream through the liquid chromatography column, the several compounds in the sample "plug" are separated into discrete bands of individual compounds, which can then be detected. If a several-compound-containing sample were injected as a continuous flow into a liquid chromatography column, no discrete bands would emerge. Rather, the output would be a mixture not unlike the sample that was inserted into the upstream end of the liquid chromatography column.

The temporal resolution of an experiment wherein the sample is withdrawn from a living organism through a microdialysis technique is determined by a combination of the perfusion rate of the compound of interest through the microdialysis probe, and the sample volume requirement of the particular analytical technique. As such, the greater the volume of analyte required for the particular analytical technique, the slower the temporal resolution.

By necessity, microdialysis samples are aqueous. The analytes sought to be detected typically have a small molecular weight, and a moderate to high water solubility. For these reasons, liquid chromatography has been the most popular analytical technique to couple with microdialysis sampling for separating out the various compounds of interest within the microdialysis sample. However, even with the use of very small diameter (e.g. 1 mm) microbore columns, most liquid chromatography techniques require at least one microliter of sample to perform the necessary separation and detection operations.

Typically, microdialysis sampling uses a very slow perfusion rate, such a 1 microliter per minute. At such a rate, the maximum temporal resolution when using a liquid chromatograph requiring 1 micro liter of sample is only 1 detectable sample per minute. Theoretically, higher perfusion rates can be used to generate larger sample volumes per unit of time, and thus theoretically reduce the maximum temporal resolution. However, higher perfusion rates may often not reduce the effective temporal resolution, as higher perfusion rates usually result in the sample having a lower concentration of the analyte of interest, thereby placing a strain on the detection limits of the analytical method.

Certain other methods exist that require smaller sample volumes than liquid chromatography. One such analytical method is capillary electrophoresis, in which sample volumes of a few nanoliters are usually sufficient. Because of its smaller volume requirements, the use of capillary electrophoresis with microdialysis can provide improved temporal resolution, when compared to liquid chromatography.

It is known that microdialysis samples can be analyzed by capillary electrophoresis. See, O'Shea, Telting-Diaz, Lunte and Lunte *Electroanaly.* 1992, Volume 4 at Pages 463, 468; O'Shea, Weber, Bammel, Lunte, Lunte and Smith, *Chromatographer,* 1992, Volume 608 at Pages 189-195; and Tellez, Forges, Roussin, and Hernandez, *J. Chromatogr. Biomed. Appl.,* 1992, Volume 581 at Pages 257-266. These known earlier studies used an off-line collection of the microdialysis sample, and a subsequent analysis by capillary electrophoresis. Typically, five microliters of the dialysate was collected for analysis. However, of the five microliters collected, only five nanoliters were ultimately injected into the capillary electrophoresis detection system. The reason that a quantity greater than five nanoliters was collected is due to the difficulties involved in quantitatively handling volumes less than one microliter in off-line systems. In particular, evaporation creates significant problems.

One advantage with the use of microdialysis sampling is that the dialysate (the sampling material and the fluid that passes through the microdialysis membrane) is protein-free and suitable for direct injection into either a liquid chromatography column or into a capillary electrophoresis system. By coupling the microdialysis sampling to an analytical separator/detector in an on-line fashion, it may be possible to avoid the problems of sample manipulation discussed above. To this end, on-line microdialysis sampling has been described as being coupled to liquid chromatography, flow injection analysis, and mass spectrometry. See Damsma, Westernik, DeVreis, Van den Berg, and Horn, *J. Neurochem* 1987, Volume 48 at Pages 15-23—15-28 (liquid chromatography); Church and Justice *Anal. Chem.,* 1987, Volume 59 at Pages 7-12 through 7-16 (liquid chromatography); Boutelle, Fellows, and Cook, *Anal. Chem.,* 1992, Volume 64 at Page 1790 through 1794 (flow injection analysis); and Caprioli and Lyn, *Proc. Natl. Acad. Sci. U.S.A.,* 1990, at Pages 240-243 (mass spectrometry).

With the on-line systems discussed above, to the applicant's knowledge, the best temporal resolution achieved by any of the techniques has been two minutes.

Capillary electrophoresis systems have also been coupled to liquid chromatography in a multi-dimensional separation system, and to a flow injection analysis (FIA) system. See Bushey and Jorgenson, *Anal. Chem.,* 1990, Volume 62 at Pages 978-984 (multi-dimensional separation system); Jorgenson and Bushey U.S. Pat. No. 5,131,998; and Tsuda and Zare, *J. Chromatogr.,* 1991, Volume 559 at Pages 103-110. However, none of the systems described above is suitable to couple a microdialysis sampling system to a capillary electrophoresis detection system. It is therefore one object of the present invention to provide a means for coupling a capillary electrophoresis detection system to a sequential, multiple sample acquisition device such as a microdialysis or ultrafiltration sampling system.

SUMMARY OF THE INVENTION

In accordance with the present invention, an interface is disclosed for use with a sequential multiple sample acquisition device and a capillary electrophoresis device. The interface unit comprises a body member having a base and an upstanding wall that defines a generally hollow interior well. The upstanding wall includes an inlet passageway and an outlet passageway. An inlet guide member is provided that has an axially extending guide passageway disposed coaxially with the inlet passageway. An outlet guide member is provided that has an axially extending guide passageway disposed coaxially with the outlet passageway. An inlet capillary tube means has an outer diameter sized for being received by the axially extending guide passageway of the inlet guide member, and a fluid passageway through which analyte can flow. Additionally, the inlet capillary tube means includes a first end disposed exteriorly of the well and a second end disposed within the well. The interface also includes an outlet capillary tube means having an outer diameter sized for being received in the axially extending guide passageway of the outlet guide member, a fluid passageway through which analyte can flow, a first end disposed within the well and a second end disposed exteriorly of the well.

Preferably, the interface is used in conjunction with a valve for collecting analyte from a microdialysis sampling system, and for dispensing a discrete analyte plug to the interface system. The valve includes a collection port for receiving a generally continuous flow of analyte from the analyte source, and a dispensing port for dispensing analyte from the valve. A transfer container means is provided for transferring a discrete analyte plug from the collection port to the dispensing port. A flushing agent receiving means is provided directing a stream of flushing agent to the dispensing port.

Additionally, the device is constructed so that the valve and interface electrically isolate the animal from which the microdialysis sample is being obtained from the high voltage associated with the capillary electrophoresis separator and detector. Further, the inlet and outlet capillary tubes are placed in an adjacent coaxial relation, wherein the downstream (second) end of the inlet capillary tube is placed adjacent to the upstream (first) end of the outlet capillary tube to facilitate the flow of a portion of the analyte plug from the inlet capillary tube to the outlet capillary tube. The well preferably contains a sufficient volume of capillary electrophoresis running buffer to flush the area between the inlet and outlet capillary tubes with running buffer, thereby helping to reduce the likelihood of undesired analyte entering into the outlet capillary tube means where the capillary electrophoretic separation is occurring.

One feature of the present invention is that the interface and valve arrangement of the present invention permits a capillary electrophoresis separation and detection system to be coupled to a time sequential, multiple sample acquisition technique (or device), such as a microdialysis or ultrafiltration probe. This feature has the advantage of permitting the researcher to detect the presence of compounds of interest that are obtained in a generally continuous basis from living organisms, from smaller sample volumes than was previously possible. This feature has the additional advantage of permitting the researcher to increase the temporal resolution (and hence increase the number of data points available) from a particular sample, or perform the dialysis experiment at lower flow rates and get better recovery. This increased number of data points helps to give the researcher a more complete understanding of the activity of the compound of interest within the living organism.

Another feature of the present invention is that means are provided for electrically isolating the capillary electrophoresis device from the sample acquisition device, and hence the living organism to which the sample acquisition device is attached. This feature has the advantage of better enabling the device to be used in conjunction with sample acquisition devices (such as microdialysis and ultrafiltration devices) that are coupled to a living organism. Absent the electrical isolation, the voltage and/or current used to conduct the capillary electrophoretic separation would likely have a deleterious effect on the laboratory animal. Although the microdialysis/capillary electrophoresis system has particular utility with living organisms, it is also useful in conjunction with non-animal applications such as fermentation baths, and in vitro studies of enzyme kinetics.

It is also a feature of the present invention that the interface device includes an inlet capillary tube having a downstream end that is positioned within a well of capillary buffer solution as to foster the flow into the outlet capillary of only a portion of the analyte in the inlet capillary tube means. This feature has the advantage of enabling the sample to be handled through the valve and inlet in a quantity (preferably about 60 nanoliters or less) that is large enough to maintain good quantitative consistency within the sample, but reduces the quantity of analyte at the outlet capillary tube means (where the electrophoretic separation is occurring) to a sample amount well suited for capillary electrophoretic separation.

These and other features will become apparent to those skilled in the art upon review of the detailed description of preferred embodiment of the present invention described below in conjunction with the following drawings.

DETAILED DESCRIPTION OF THE INVENTION

Figure 1:
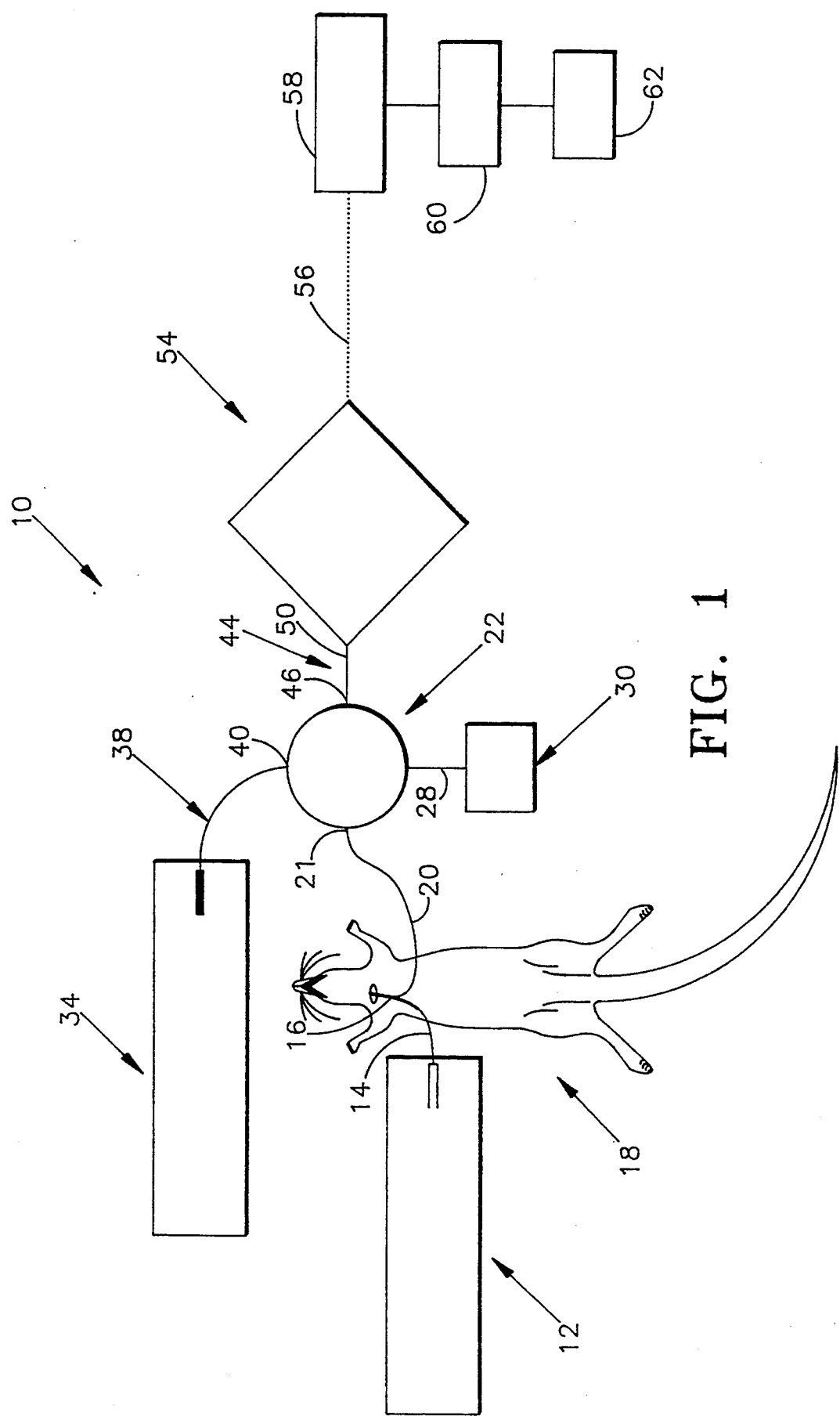
FIG. 1 is a schematic view of a microdialysis/capillary electrophoresis experimental apparatus using the present invention.

A microdialysis experimental apparatus 10 is shown in FIG. 1 as including a perfusion fluid pump 12 for pumping a microdialysis perfusion fluid through a microdialysis perfusion fluid delivery line 14 to a microdialysis probe 16. Microdialysis probe 16 is implanted in a blood vessel or fluid filled space (such as the area near the brain) of a laboratory animal such as a rat 18. Examples of suitable microdialysis probes are the model numbers CMA/10, CMA/11, or DL-3 microdialysis probes available from Bioanalytical Systems, Inc. of West Lafayette, Ind.

In a microdialysis type sample acquisition system, perfusion fluid is flowed on one side of a microdialysis membrane that is part of the microdialysis probe 16. As the microdialysis membrane is a semi-permeable membrane, various chemical compounds within the laboratory animal's extracellular fluid adjacent to the microdialysis probe 16 will migrate across the microdialysis membrane. In this way, compounds of interest from the animal are drawn across the semi-permeable membrane and into the perfusion fluid. The material that flows through the microdialysis pickup line comprises an analyte that consists of a mixture of the compounds of interest that passed through the microdialysis membrane from the laboratory animal, and the perfusion fluid pumped by the pump 12 through the probe 16.

The microdialysis pickup line 20 transports the analyte from the laboratory animal 18 to a collection port 21 of a valve means such as a microinjection valve 22. As will be described in more detail below, the valve 22 is provided for receiving a continuous flow of analyte from the microdialysis pickup line 20, selectively removing discrete "plugs" of analyte, and delivering these plugs of analyte to a dispensing port 46 of the valve 22 for transference to an interface 54. The remainder of the continuous flow of analyte received by the valve 22, that is not used as part of a "plug" is shunted by the valve 22 into a waste line 28 that conducts the unused analyte to a waste receptacle 30 in which the analyte can be disposed.

The microdialysis/capillary electrophoresis device 10 also includes a capillary running buffer pump 34 for pumping a running buffer of the type used in capillary electrophoresis. The running buffer is pumped into a buffer delivery line 38 that conducts the running buffer from the pump 34 to a running buffer receiving means 40 of the valve 22.

An analyte transfer line 44 is provided for alternatingly transferring both running buffer and analyte from the dispensing port 46 of the valve 22 to the interface 54. The downstream portion of the analyte transfer line 44 (or alternately, the entire analyte transfer line 44) can comprise an inlet capillary tube 50 of the interface 54.

The interface 54 also includes an outlet capillary tube 56. The outlet capillary tube 56 comprises the capillary tube in which the electrophoretic separation takes place. As will be described in more detail below, voltages applied to the analyte and running buffer in the outlet capillary tube 56 foster a separation of the compounds in the analyte mixture flowing through the outlet capillary tube 56. A detector 58 is disposed downstream from the outlet capillary tube 56. A controller 60 is coupled to the detector 58 for processing the information it receives from the detector 58, and for controlling the timing of the valve 22. An output device, such as a strip chart recorder 62 is coupled to the controller 60.

Figure 2:
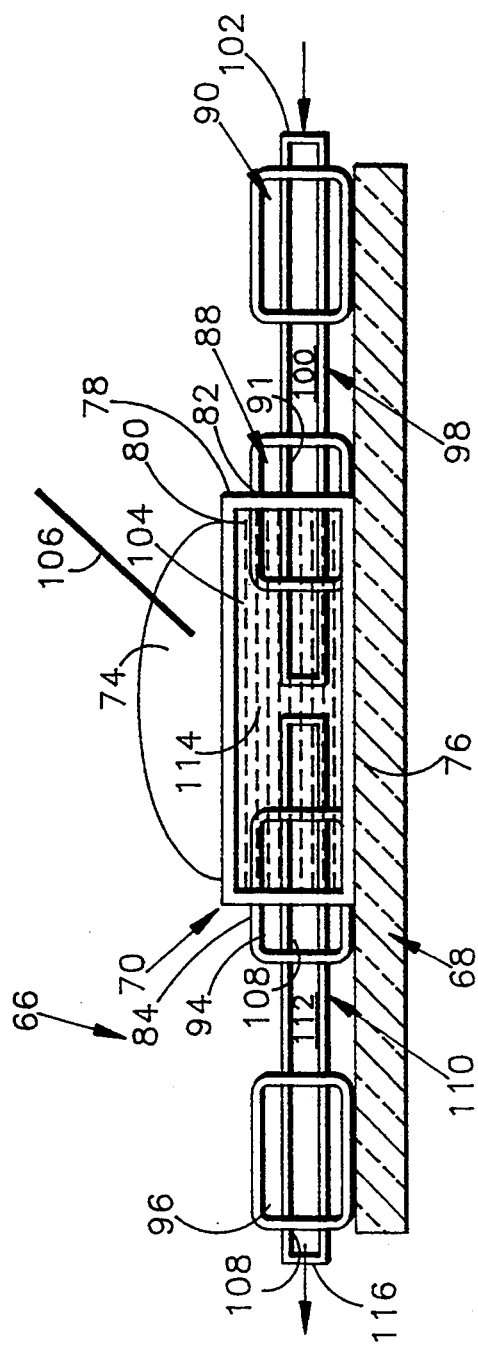
FIG. 2 is an elevational, schematic view of an alternate embodiment of the present invention.

A side elevational view of one embodiment of an interface device 66 of the present invention is best shown in FIG. 2. FIG. 2 somewhat schematically depicts the interface device 66 used in conjunction with the applicant's experiments that will be described in more detail below. The interface device 66 can be constructed of standard available laboratory materials. A "production model" interface device will be described below in conjunction with FIGS. 3–5.

Interface 66 is built upon a microscope slide 68 that serves as a support for the interface 66. A body member 70 is constructed of a non-conductive material and is designed to have a well in which a reservoir of buffer material 74 can be contained. The body member 70 includes a base, and a circumferential upstanding wall 78. The base 76 and upstanding wall 78 define an interior well 80 that holds and contains a supply of running buffer 74. The upstanding wall 78 includes an inlet passageway 82, and an outlet passageway 84. The inlet and outlet passageways 82, 84 are preferably positioned 180 degrees from each other.

The inlet passageway 82 is sized for receiving an inlet guide member 88. Inlet guide member 88 is one of a pair of inlet guide members 88, 90. Inlet guide number 88 has a radially outer surface that is sized to be received snugly within the inlet passageway 82. Each of the inlet guide members 88, 90 has an axially extending guide passageway 91 for receiving the radially outer surface of an inlet capillary tube 98.

The inlet capillary tube 98 can be the downstream end of analyte transfer tube 44. Alternately, analyte transfer tube 44 can comprise one continuous tube that is sized to serve as an inlet capillary tube 98. The inlet capillary tube 98 includes an axially extending interior fluid passageway 100 through which the analyte (the compound of interest and the perfusion fluid) can flow. The inlet capillary tube 98 has a first end 102 that is disposed exteriorly of the well 80. If the inlet capillary tube 98 is one continuous tube, the first end 102 of the inlet capillary tube 98 can be disposed at the dispensing port 46 of the valve 22. The inlet capillary tube 98 also includes a second end 104 that is disposed within the well, so that analyte flowing through the fluid passageway 100 flows from the first end 102 of the inlet capillary tube 98, to and through the second end 104, and into the running buffer 74 contained within the well 80 of the interface device 54. The relatively outwardly disposed second inlet guide member 90 is generally similar in configuration to guide member 88. The two inlet guide members 88, 90 are aligned to provide for better alignment and support of the inlet capillary tube 98 that is received by both of the inlet guide members 88, 90.

The outlet passageway 84 is sized for receiving one of a pair of outlet guide members 94, 96. Outlet guide member 94 has a radially outer surface that is received by the outlet passageway 84, and an axially extending guide passageway 108.

The two outlet guide members 94, 96 each include an axially extending guide passageway 108. The two axially extending guide passageways 108 of the two guide members 94, 96 are aligned and sized for receiving the radially outer surface of the outlet capillary tube 110. The outlet capillary tube 110 includes a fluid passageway 112 through which analyte can migrate, a first, upstream end 114 disposed within the well 80, and a second downstream end 116 disposed exteriorly of the well. A ground electrode 106 is positioned inside the well 80 and terminates exteriorly of the well 80 at a terminal (not shown).

As shown in FIG. 2, the inlet capillary tube 98 and outlet capillary tube 110 are disposed coaxially. The second end 104 of inlet capillary tube 98, and the first end 114 of the outlet capillary tube 110 are placed in an opposed, adjacent but separated relation to facilitate the flow of a portion of the analyte from the inlet capillary tube 98 into the outlet capillary tube 110. Preferably, the first end 114 of the outlet capillary tube 110 is separated from the second end 104 of the inlet capillary tube 98 by a distance of less than about 300 micrometers. As discussed above, one benefit of the present invention is that it is very well suited for detecting the presence of compounds of interest in very small samples. For example, the inlet capillary tube 98 preferably has a diameter of between about 20 and 100 micrometers, and is sized to accommodate flow rates of between about 0.5 and 10.0 microliters per minute of analyte.

Figure 5:
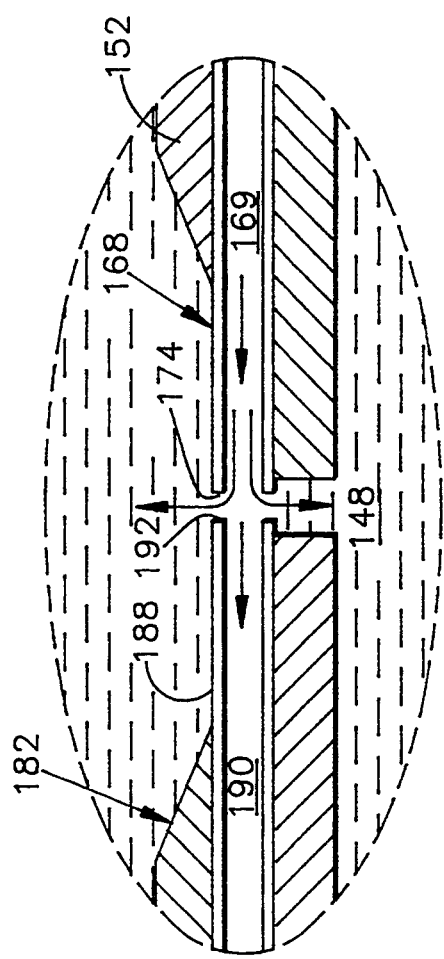
FIG. 5 is an enlarged, fragmentary, sectional view of a portion of the interface of the present invention adjacent to the area where the inlet and outlet capillary tubes are placed in proximity to each other.
Figure 4:
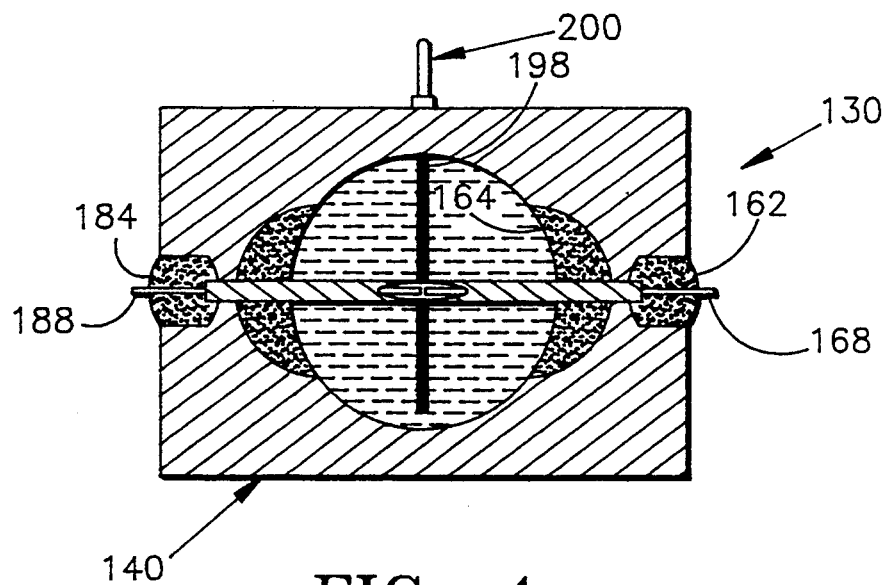
FIG. 4 is top, sectional view of the interface of the present invention.
Figure 3:
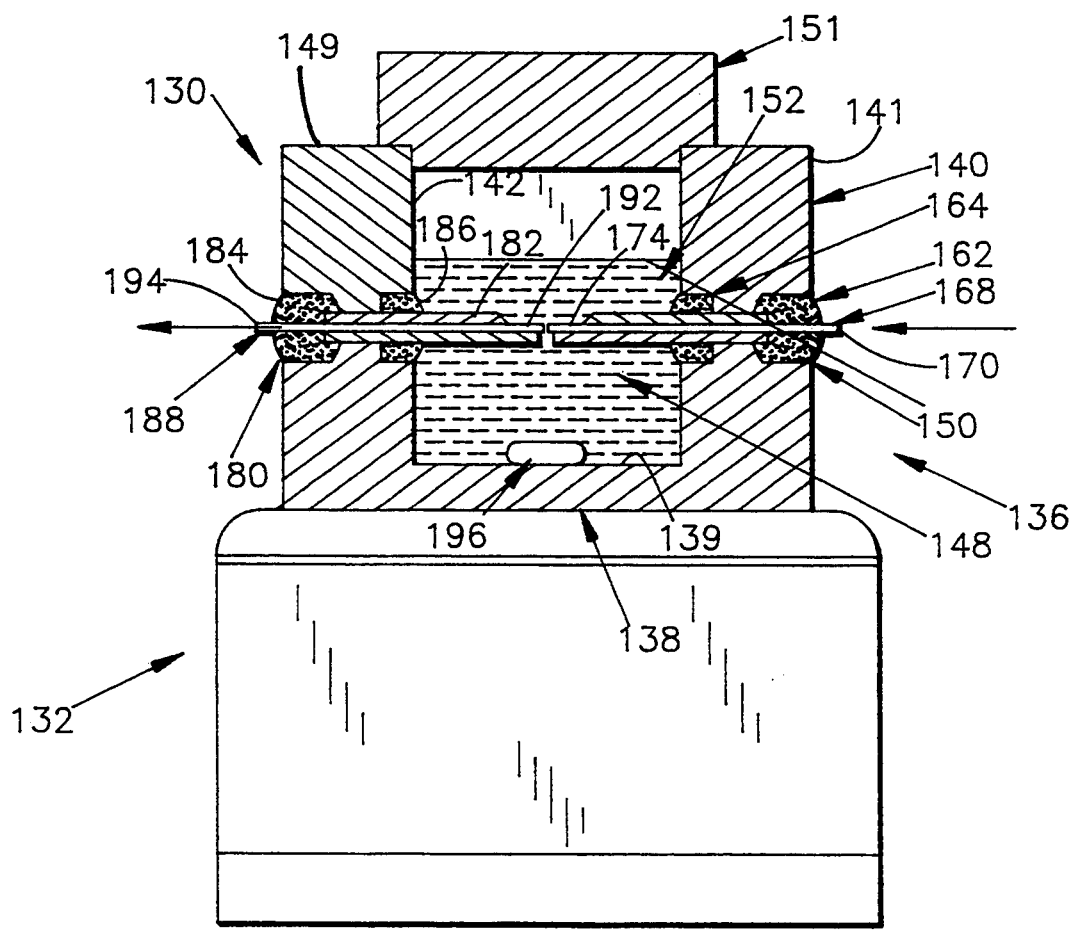
FIG. 3 is a side, sectional view of the preferred embodiment of the interface of the present invention.

A commercial, production version of the interface 130 is best shown in FIGS. 3–5 as including a body 136 made of a non-conductive material such as PEEK. The interface 130 is designed to be placeable on the upper surface of a magnetic stirring device 132. The body 136 of the interface 130 includes a base portion 138 having a lower surface that can rest on the upper surface of the magnetic stirring device 132, and an upper surface 139. The body 136 also includes an upstanding wall 140. As best shown in FIG. 4, the upstanding wall 140 can include a generally rectangular (in cross section) radially outer surface 141, at a generally circular (in cross section) radially inner surface 142. The radially inner surface 142 of the upstanding wall 140, and the upper surface 139 of the base portion 138 define an interior well 148 of the interface 130. Preferably, the well 148 can hold between about 1 and 6 milliliters of the capillary electrophoresis running buffer, and is generally cylindrical in shape.

The upstanding wall 140 terminates at a lip 149 at its top. Lip 149 defines a top opening of the well 148. A cap 151 is threadedly engagable with the lip 149 to enable the user to selectively open and close the top opening of the well 148, to permit the user to add or withdraw running buffer solution.

The interface device includes an inlet passageway 150 that is sized for receiving an inlet guide member 152. The inlet guide member 152 includes an axially extending guide passageway that is disposed generally coaxially with the inlet passageway 150, and is sized for receiving an inlet capillary tube 168.

The inlet passageway 150 includes a first enlarged portion adjacent to the radially outer surface 141 of the wall 140. An adhesive mass 162 is placed in the first enlarged portion to adhesively fixedly couple the inlet guide member 152 to the inlet passageway 150. The inlet passageway 150 also includes a second enlarged portion disposed adjacent to the radially inner surface 142 of the wall 140. An adhesive mass 164 is placed into the second enlarged portion for further helping to anchor the inlet guide member 152 to the inlet passageway 150 (and hence wall 140).

As best shown in FIG. 3, inlet guide member 152 preferably comprises an elongated tube that extends coaxially with the inlet capillary tube 168, for a substantial portion of the inlet capillary tube's 168 length within the inlet passageway 150 and well 148. As best shown in FIG. 5, the inlet guide member 152 terminates just short of the second end 174 of the inlet capillary tube 168. The inlet capillary tube 168 includes a first end 170 disposed exteriorly of the well 148, and a second end 174 disposed within the well. The inlet capillary tube 168 can be a single capillary tube that extends between the valve 22 and the interface 130. The inlet capillary tube 168 also includes a fluid passageway 169 through which analyte can flow into the well 148 of the interface 130.

The inlet capillary tube 168 has an outer diameter sized for being slidably received by the axially extending passageway of the inlet guide 152. The inlet capillary tube sized to be slidably received the axially extending passageway of the inlet guide member 152 to foster the quick addition and replacement of capillary tubes within the interface 130. Although the inlet capillary tube should be sized to be slidably received within the axially extending passageway of the inlet guide 168, the fit there-between should be significantly snug so as to reduce leakage out of the well 148 caused by flow of running buffer (or analyte) between the outer surface of the inlet capillary tube 168 and the inlet guide member 152.

The upstanding wall 140 also includes an outlet passageway 180 that is preferably disposed to be coaxially with, and 180 degrees separated from the inlet passageway 150. The outlet passageway 180 receives an outlet guide member 182 that has an axially extending guide passageway disposed coaxially with the outlet passageway 180. The outlet passageway 180 includes a first enlarged portion adjacent to the radially outer surface 14 1 of the wall 140 for receiving a first adhesive mass 184. The outlet passageway 180 also includes a second enlarged portion adjacent to the radially inner surface 142 of the wall 140 for receiving a second adhesive mass 186. The first and second adhesive masses 184, 186 are provided for fixedly coupling the outlet guide member 182 in the outlet passageway 180.

An outlet capillary tube means 188 is provided that has an outer diameter sized for being slidably received by the axially extending passageway of the outlet guide member 182. The outlet capillary tube means 188 also includes an interior fluid passageway 190 through which analyte can flow from the well 148 to the detector 58. The outlet capillary tube 188 includes a first end 192 disposed within the well 148, and a second end 194 disposed exteriorly of the well. The first end 192 of the outlet capillary tube 188 is disposed in an opposed, adjacent but separated relation to the second end 174 of the inlet capillary tube 168 to foster the flow of a portion of the analyte from the inlet capillary tube fluid passageway 169, into the fluid passageway 190 of the outlet capillary tube 188.

As best shown in FIG. 5 (and described in more detail below), analyte flowing from the first end 170, toward the second end 174 of the inlet capillary tube 168 enters into the small space between the second end 174 of the inlet capillary tube 168 and the first end 192 of the outlet capillary tube 188. In this small (generally less than 300 micrometers) space, portions of the analyte that flow out of the fluid passageway 169 of the inlet capillary tube 168 will flow into the well 148, and towards the outlet capillary tube 188. However, because the second end 174 of the inlet capillary tube 168 and the first end 192 of the outlet capillary tube 188 are placed in such approximate, opposed relation, a portion of the analyte that emerges from the fluid passageway 169 can be injected electrokinetically into fluid passageway 190 of the outlet capillary tube 188.

The outlet capillary tube 188 has an outer diameter sized to be received by the outlet guide member 182 for the same reasons as were discussed above in connection with the relative sizing of the inlet capillary tube 168 and the inlet guide member 152.

Returning now to FIG. 3, the inlet guide member 152 and outlet guide member 182 position the inlet capillary tube 168 and outlet capillary tube 188 at a sufficient distance above the upper surface 139 of the base 138, to permit a magnetic stirring rod 196 be placed within the well 148. The magnetic stirring rod 196 can rest upon the upper surface 139 of the base 138, and can be rotated by the magnetic stirrer 132. This rotation helps to maintain the capillary running buffer within the well 148 in a well mixed condition to prevent the build up of any concentrations of analyte or compounds of interest in any portions of the well 148.

An electrode 198 is positioned inside the well 148, and terminates exteriorly of the interface 130 at a terminal 200. Terminal 200 can be coupled to a suitable cable. The ground side of the electrophoresis experiment is generally located at the interface 130 so that the high voltage will not exist at the valve or at the animal. This is important for safety as well. The ground is referred at the interface because of the fact that the capillary electrophoresis system is always "on".

The structure and operation of the valve 22 used in connection with the electrophoresis apparatus of the present invention is best described with reference to FIGS. 6–9.

A valve 220, such as a model E2NI4W-06 valve manufactured by Valco Instruments of Houston, Tex., includes a generally stationary body 222, and a movable turntable 226. The valve 220 also includes a collection port 228 for collecting analyte from the laboratory animal 18. The valve 220 further includes a dispensing port 232 for dispensing analyte and capillary electrophoresis (CE) running buffer from the valve 220 to the interface 54, CE capillary 56 and detector 58.

The movable turntable 226 is generally rotatably movable relative to the stationary body 222, and includes four sample loops including a first sample loop 236, a second sample loop 240, a third sample loop 242 and a fourth sample loop 244. The sample loops 236, 240, 242, 244 function as transfer containers, because they are designed for containing a volume of material (e.g., 60 nanoliters of analyte) and for transferring that contained volume of material between the collection port 228 and the dispensing port 232.

The size of the sample loops 236, 240, 242, 244 is dictated by the volume of material required for a particular experiment, and the detection apparatus. As capillary electrophoresis only requires small volumes of sample, the sample loops 236, 240, 242, 244 are necessarily small. Actually, the size of the sample loops (generally around 60 nanoliters) is greater than the volume of sample required for capillary electrophoresis. However, handling and reliability problems would exist if the sample loops 236, 240, 242 and 244 were as small as the actual sample required. If these handling and reliability problems could be overcome, a sample size loop of less than 60 nanoliters would be acceptable, and possibly preferable.

The collection port 228 includes an analyte receiving tube 248 that conducts analyte from the microdialysis pickup line to the particular sample loop (236 in FIG. 6, 244 in FIG. 7) that is positioned at the dispensing port 228. An analyte discarding tube 250 is provided for conducting analyte away from the sample loop (e.g., 236 in FIG. 6) to a waste receptacle 30.

The dispensing port 232 includes a flush agent receiving means 254 for conducting CE running buffer (which also serves as a flushing agent) from the second pump 34 to the sample loop (e.g., second sample loop 240 in FIG. 6) positioned at the dispensing port 232. A transfer tube 256 is provided for conducting material from the sample loop (e.g., 240 in FIG. 6) to the inlet capillary tube 50 of the interface.

It is important to understand that during the conduct of an experiment, all of the microdialysis pickup line 20, sample loop positioned at the collection port (e.g., 236), analyte discarding tube 250, flushing agent receiving means 254, sample loop positioned at the dispensing port 232 (e.g., sample loop 240), transfer tube 256, microdialysis inlet capillary tube 50, capillary interface 54, and outlet capillary tube 56 are always filled with fluid. For the sake of clarity, those portions of the device (elements 20, 248, 236 and 250 in FIG. 6) that are filled with analyte are indicated by "hatching". Those portions of the device (elements 256, 240, 254, 50, 54 and 56 in FIG. 6) that are filled with capillary running buffer are shown as being "clean".

The operation of the valve 220 will now be discussed.

Figure 6:
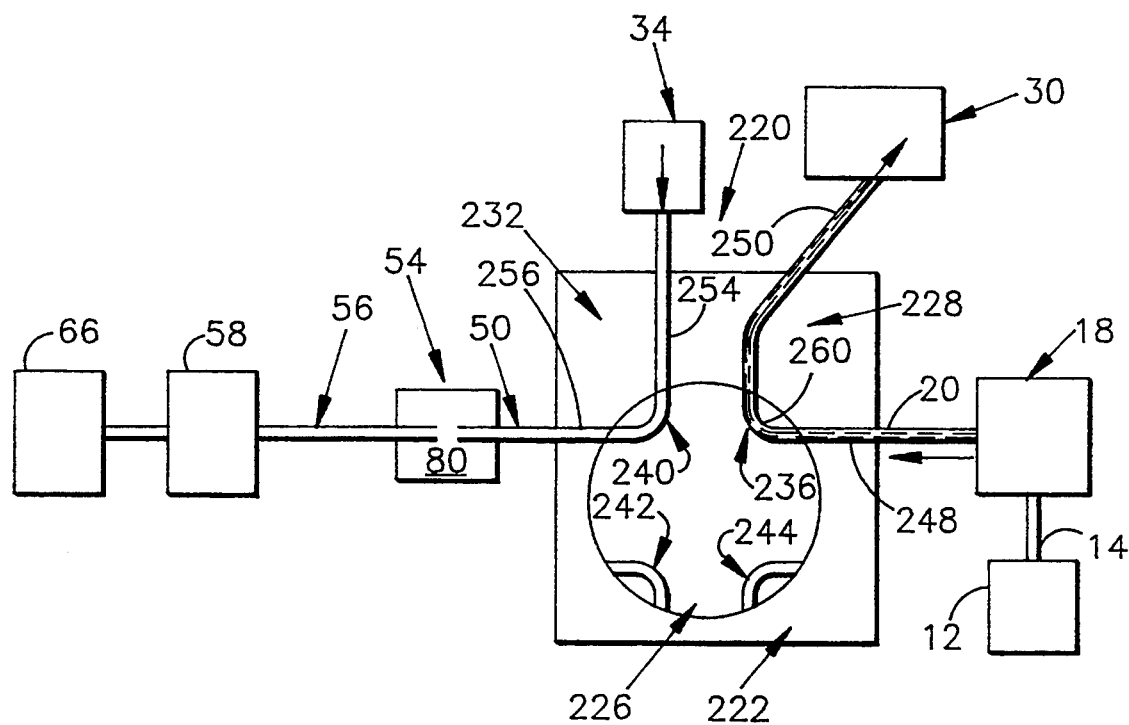
FIGS. 6–9 are schematic, sequential views of a microdialysis experimental apparatus incorporating the present invention, illustrating the operation of the present invention.

FIG. 6 represents the apparatus at a point before any analyte is delivered to the capillary interface 54. When the device is completely assembled, and the microdialysis probe is attached to a laboratory animal 18, such that the analyte begins flowing from the animal 18, the analyte is directed to the microdialysis pickup line 20, until it entirely fills the analyte receiving tube 248, first sample loop 236 and analyte discarding tube 250. Simultaneously, CE running buffer is pumped by the second pump 34 into the flushing agent receiving means 254, through the second sample loop 240, through the transfer tube 256 into the inlet capillary tube 50, the interface 54, and electrokinetically pumped into the capillary electrophoresis system via the outlet capillary tube 56. At any time after all the various components are filled with fluid, the turntable 226 can be rotated 90° (here shown as counterclockwise) to position the device in the position shown in FIG. 7. When so rotated, the analyte contained within the first sample loop 236 is rotated to the dispensing port 232.

It will be noted that the first sample loop 236 contains a "plug" of analyte 260. The plug 260 represents a discrete amount of analyte that is placed within a stream of CE running buffer, and is surrounded both upstream (in flushing agent receiving means 254) and downstream (in transfer tube 256) by CE running buffer. It will also be noted that the fourth sample loop 244 has been rotated so that it is now positioned in the collection port 228. Although the fourth sample loop 244 is shown as containing analyte, when it is first rotated into the first collection port 228, it will be filled with capillary running buffer. However, the capillary running buffer within sample loop 244 will be displaced quickly by analyte being delivered to the fourth sample loop 244 through the analyte receiving tube 248.

Figure 8:
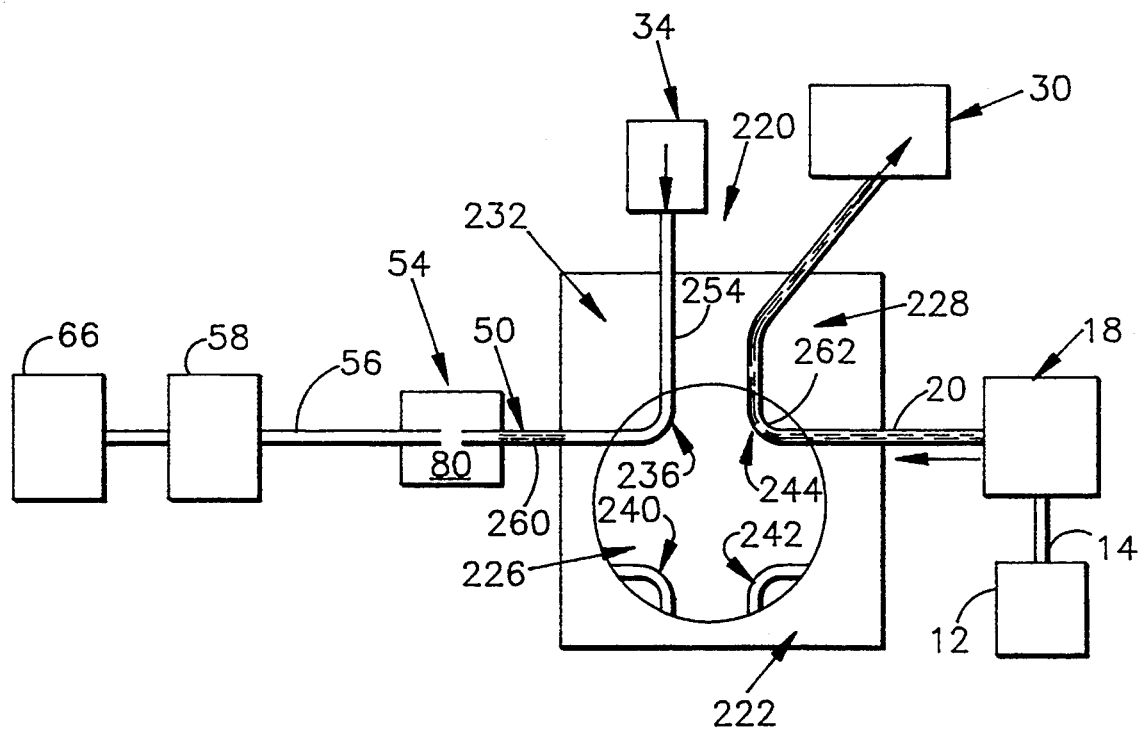

Turning now to FIG. 8, the constant infusion of the CE running buffer through the flushing agent receiving means 254 causes the plug of analyte 260 to transfer out the transfer tube 256 and into the inlet capillary tube 50. In FIG. 8, one can gain a better appreciation of the discrete volume, "plug" nature of the analyte plug 260.

Figure 7:
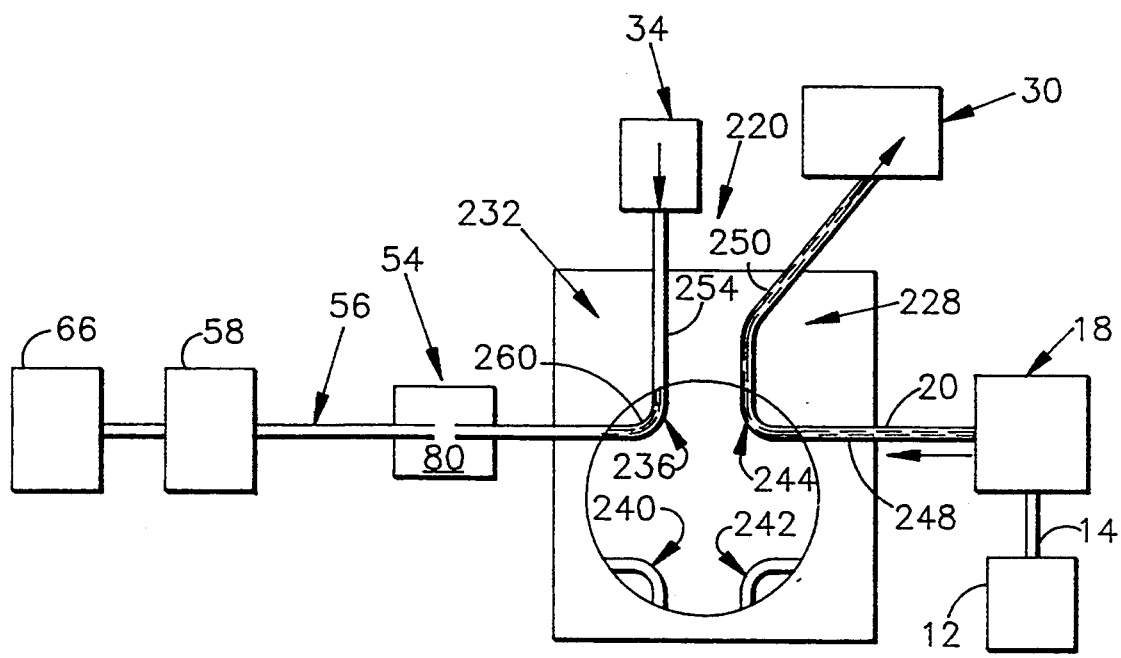

It should also be noted that FIG. 8 shows the various sample loops 236, 240, 242 and 244 in their same relative rotational position as in FIG. 7, FIG. 8 also shows the first analyte plug 260 being in the inlet capillary tube 50, approaching the interface 54.

Figure 9:
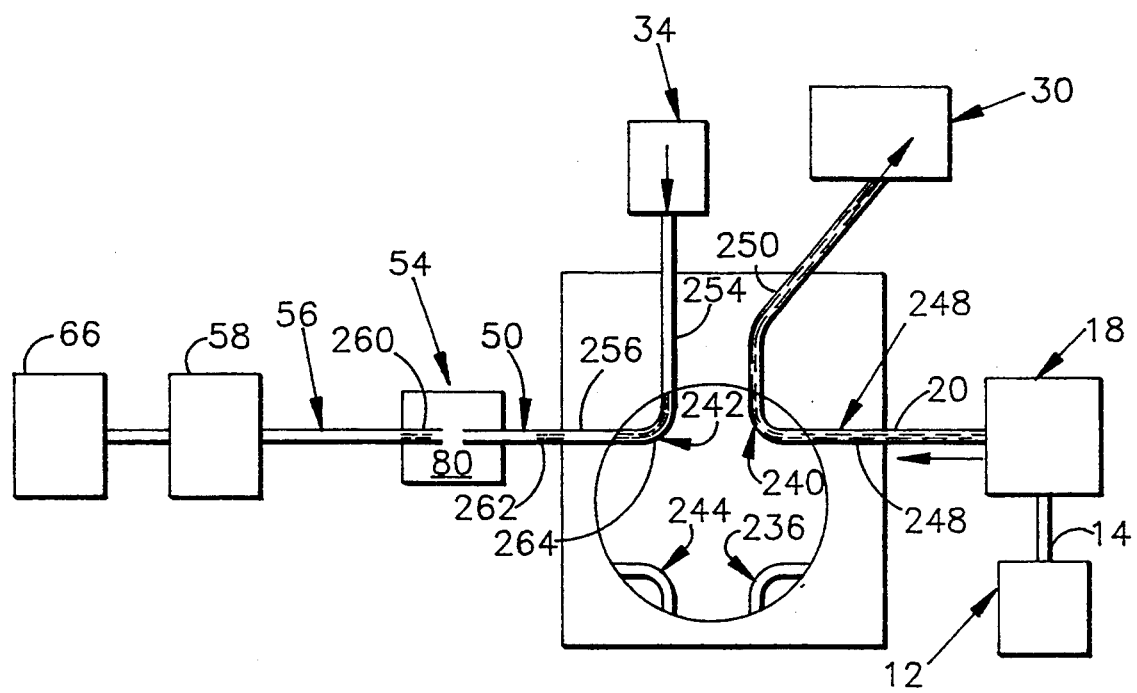

Your attention now is directed to FIG. 9 that depicts the valve 220 having been rotated through two incremental positions. For example, sample loop 236 is disposed in FIG. 9 at 180° from its position shown in FIG. 8. In the interval between the time period of FIG. 8 and that of FIG. 9, the plug of analyte 262 contained in sample loop 244 (FIG. 8) has been delivered into the transfer tube 256. Additionally, first analyte plug 260 has advanced through the interface 54, so that a portion of the analyte plug 260 is now in the outlet capillary tube 56, and undergoing electrophoretic separation therein.

In FIG. 8, sample loop 242 is shown as being in the "on deck" position. In the interval between FIG. 8 and FIG. 9, sample loop 242 has been rotated through the collection port 228, where it became filled with analyte, and further rotated to the dispensing port 232, where it is shown in FIG. 9. The CE running buffer being pushed through flushing agent receiving means 254 will push the third plug of analyte 264 out of sample loop 242, and into a transfer tube 256.

This sequence of events continues to occur, and results in several discrete plugs of analyte (e.g., 260, 262, 264) being disposed at spaced intervals within the capillary electrophoresis outlet capillary tube 56, the inlet capillary robe 50, and the transfer robe 256.

Figure 10:
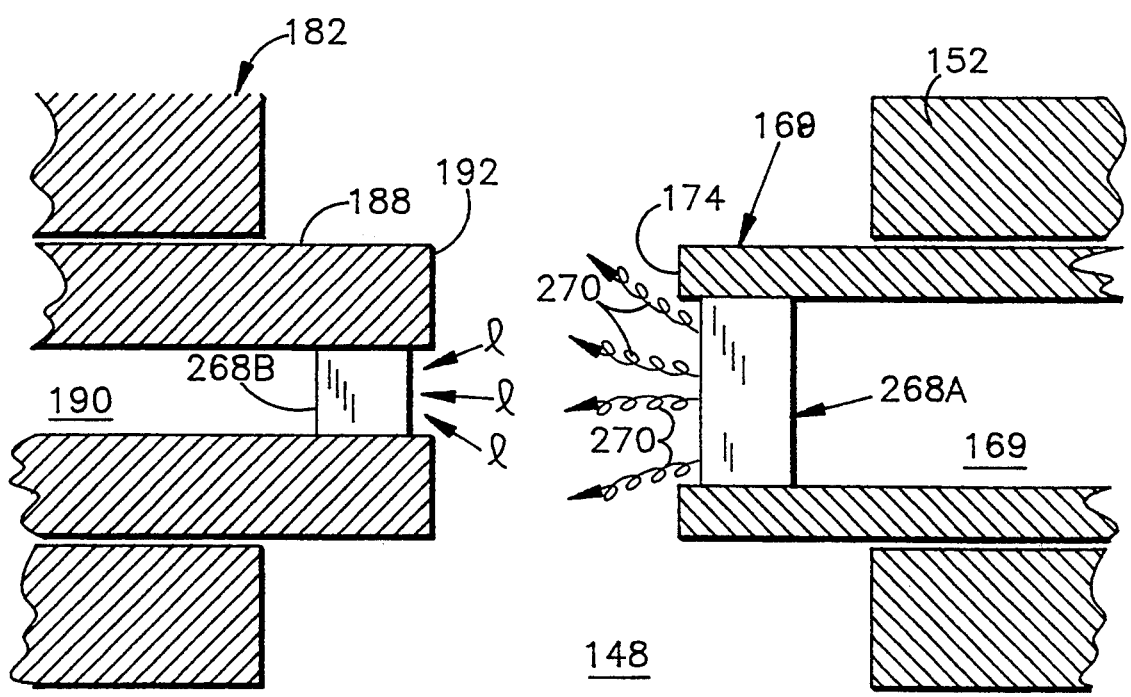
FIG. 10 is a schematic view of the juncture of the inlet and outlet capillary tubes within the well of the interface of the present invention.

Turning now to FIG. 10, the operation of the flow of analyte through the interface 130 will be disclosed. FIG. 10 shows a greatly enlarged version of the portion of the interface 130 where the second or downstream end 174 of the inlet capillary tube 168 meets the first or upstream end 192 of the outlet capillary tube 188. Two portions 268A and 268B of an analyte plug are shown, with portion 268A being disposed adjacent to the second end 174 of the inlet capillary tube 168, and plug portion 268B being disposed adjacent to the first end 192 of the outlet capillary tube 188. As the analyte plug 268 is pushed out the second end 174 of the inlet capillary tube 168, the molecules within the analyte plug tend to become dispersed within the well, as shown by arrows 270. However, due to the close proximity of the entrance end 192 of the outlet capillary 188, a fractional portion of the incoming analyte plug 268A will cross the gap between the inlet robe 168 and the outlet tube 188 and form a smaller, outgoing analyte plug 268B.

An electro-osmotic flow is induced within the flow path 190 of the outlet capillary robe 188 by the high voltages used in the adjacent electrophoretic separation area 56 (seen in FIG. 1) so that fluid is continuously drawn from the well into the outlet tube 188. This fluid will be an analyte plug 268B when a sample of analyte 268A is flowing from the inlet tube 168 or merely buffer solution during the time between samples of analyte. Due to the relatively larger volume of buffer in the well 148 (as compared to the volume of the analyte plug 268), molecules from the analyte plug 268 that are not drawn into the analyte plug portion 268B, tend to be swept away from the area between the respective ends 174, 192 of the inlet and outlet capillary tubes 168, 188. This helps to avoid a continuous flow of analyte molecules into the flow passageway 190. As discussed above, such a continuous flow would be undesirable.

Presented below is a working example and further discussion of how the various parameters and components of the device can be altered to achieve different results.

WORKING EXAMPLE AND DISCUSSION OF EXPERIMENTAL RESULTS

A. Reagents

3-Amino-1,2,4-benzotriazine-1,4-di-N-oxide (SR 4233) and 3-amino-1,2,4-benzotriazine-1-N-oxide (SR 4317), which were gifts from Sterling Drug (Rochester, N.Y.). Sodium dodecyl sulfate was obtained from Aldrich (St. Louis, Mo.). All other chemicals were reagent grade or better and used as received.

B. Capillary Electrophoresis System

The Capillary Electrophoresis (CE) system consisted of a CZE 1000r high voltage power supply manufactured by Spellman of Plainview, N.Y. Capillaries of 50 $\mu$m i.d., 360 $\mu$m o.d. (PolymicroTechnologies, Phoenix, Ariz.) having a total length of 40 centimeters and a length from injection to detection of 15 centimeters were used. A timer box was used to make off-line electrokinetic injections. The injection end of the capillary was grounded and the detection end held at a large negative potential. The high potential end was housed in an isolation box. The CE running buffer consisted of 100 mM sodium phosphate buffer, pH 6.8, with 40 mM sodium dodecyl sulfate (SDS) as a micellar additive. Columns were flushed with 0.1M NaOH prior to use. A run potential of −25 kV was used to achieve separation.

Coupled CE columns were constructed to permit high speed micellar electrokinetic chromatography (MEKC) separations. A 25 centimeter section of polyethylene tubing (0.8×1 mm.) was glued onto the CE (outlet) capillary 5 centimeters past the detection point. The polyethylene tubing was then filled with running buffer and inserted into the buffer reservoir in the high voltage isolation box. High voltage can thus be applied across very short sections of capillary without a loss of voltage gradient.

Detection of the compounds of interest in the analyte was performed by laser induced fluorescence (LIF) using a He-Cd laser (Model 4300, manufactured by Liconix of Santa Clara, Calif.) with 5–7 mW of power at 442 nm for excitation. A 442 nm interference prefilter (Edmund Scientific) was used for rejection of laser plasma. A 1 centimeter focal length biconvex lens (Melles Griot) was used to focus the beam within the capillary. A 20× microscope objective (Edmund Scientific, Barrington, N.J.) was used to collect the fluorescent image within the capillary. The image was filtered spatially through the use of an aperture placed at the image focal plane to reject scattered light collected from the capillary walls. The image was then filtered spectrally with a long-pass filter (520 nm, Schoeffel) and an interference filter (580 nm, Melles Griot). The photomultiplier was a model RI 527 manufactured by Hamamatsu of Bridewater, N.J. The photomultiplier was operated at a voltage of −1000V supplied by a Model 227 regulated power supply, manufactured by Pacific Photometric.

Data collection was accomplished with an integrated hardware/software package (Chemresearch Software version 2.4, manufactured by ISCO of Lincoln, Nebr.) running on a Tandon AT compatible microcomputer. The 12 bit board collected data at 20 hertz and controlled the valve switching. Signal amplification, variable offset and RC filtering (typically 300 milliseconds) was accomplished with a locally constructed circuit.

C. Microdialysis System

Microdialysis was carried out using a CMA 100 microinfusion pump from Bioanalytical Systems, Inc./CMA (West Lafayette, Ind. coupled to a flexible microdialysis probe. The microinfusion pump was operated at a flow rate of 1 µL/minute. The dialysis membrane was a cellulose fiber with 232 µm i.d., 250 µm o.d., and a molecular weight cutoff of 5,000 daltons. Such fibers are available from Dow Chemical of Midland, Mich. Connection from the microinjection pump to the microdialysis probe was made with 120 µm i.d. teflon tubing.

D. On-Line Microdialysis to CE Interface

The interface between the microdialysis system and the CE system must perform three functions. First, the continuous microdialysis samples must be converted to discrete samples for electrophoretic analysis. Second, the microdialysis flow rate must be converted to a rate compatible with CE. Third, the rat must be protected from the high voltages associated with the capillary electrophoresis. These functions are performed by different components of the interface. The dialysate is sampled using a microinjector for liquid chromatography while the flow conversion is accomplished by an injection interface shown in the Figures. The animal is protected by placing the interface and valve at ground.

The sampling valve was an electrically actuated internal sample loop HPLC valve (Model E2M4W-06 manufactured by Valco instruments, Houston, Tex.) with a 60 nanoliter internal sample loop. Transfer of the sample occurred continuously from the microinfusion pump to the valve. The transfer flow rate was varied between 1 to 10 µL/minute with the optimum found to be 5 µL/minute. A 26 cm length of 50 µm i.d. fused silica tubing was used as a transfer line 44 from the microinjection valve 22 to the injection interface 54.

As shown in FIG. 2, the injection interface 66 consisted of a reservoir well 80 containing the electrophoretic run buffer 74 into which fused silica inlet 98 and outlet 110 capillaries entered from opposite sides (FIG. 2). The outlet capillary 110 was the CE capillary column and the inlet capillary 98 was the transfer line from the microinjection valve 22. The capillaries 98, 110 were aligned such that the out flow of the transfer capillary 98 impinged directly on the inlet of the CE capillary 110. Reproducible alignment of the two capillaries 98, 110 in the injection interface 66 was accomplished by the use of four guide tubes 88, 90, 94, 96 permanently secured in place following pre, alignment. Four 5 millimeter lengths of 0.5×1.5 mm. polyethylene tubing (available from Alltech) were cut for use as alignment guides. These guides 88, 90, 94, 96 were placed over a 7 cm section of 360 micron o.d. capillary to align the guide tubes 88, 90, 94, 96. The assembly was placed on a microscope slide 68 with the center two guide tubes 88, 94 separated by 2 centimeters and the outer guide tubes 90, 96 separated by 4 centimeters. The guide tubes were permanently attached to the microscope slide 68 with epoxy. After all of the guides 88, 90, 94, 96 were fixed in place, the length of capillary used for initial alignment was removed. Epoxy was then used to build the buffer reservoir with dimensions of 2 cm×2 cm and sufficient depth to cover the guide tubes 88, 90, 94, 96 and capillaries 98, 110.

The inlet capillary 98 from the microinjection valve 22 was brought into one side of the injection interface 66 through two of the guide tubes 88, 90 and positioned so its second end 104 was at the midpoint of the buffer reservoir 80. Epoxy applied to the capillary behind the rear guide tube 90 fixed the position of the inlet capillary 98. The CE (outlet) capillary 110 was brought into the interface 66 through the remaining two guide tubes 94, 96 after having been aligned and fixed with respect to the detection optics. The alignment of the outlet capillary 110 in two dimensions with respect to the inlet capillary 98 was controlled by the guide tubes 94, 96. The gap between the capillaries was established manually with the use of an 8× magnifier available from Radio Shack. The precise gap distance between the inlet capillary 98 and the outlet (CE) capillary 110 can be measured optically with a measuring reticle. Estimation of the gap distance by comparison with the known diameter of the outlet capillary 110 produced good results in non-critical cases. Once correctly positioned, the outlet capillary 110 was permanently affixed to the outer guide tube 96 with epoxy.

E. Probe Characterization

It was necessary to determine the recovery characteristics of the microdialysis probe in order to determine the in vivo concentrations of SR 4233. This was done by placing the dialysis probe (not shown) in stirred solution of known concentration of SR 4233 maintained at 37° C. The microdialysis probe was perfused at 1 µL/min and samples were collected in the loop (e.g., 236) of the sampling valve 222. These were injected automatically into the interface and outlet capillary tube, which had been previously calibrated with known concentrations of standards by flow injection analysis. Recovery was calculated at several concentrations within the dosing range used and was found to be independent of concentration. The recovery value for a given probe was then used to calculate the sample concentrations from the dialysate concentrations for microdialysis sampling experiments.

F. In Vivo Pharmacokinetics

Male Sprague-Dawley rats weighing 0.39–0.43 kg were used as the living organism in which the experiments were run. The rats were anesthetized with a 3:1 mixture of ketamine/xylenol injected prior to the insertion of the probe. In this instance, a PE-50 dosing cannula was implanted into the jugular vein opposite the vein in which the microdialysis probe was implanted. The implanted probe was perfused with Ringer's solution at a flow rate of 1 µL/min. Dialysis samples were collected for intervals of 90 to 120 seconds. Blanks were collected from the animal for at least one hour prior to dosing. The animals were then administered 4 mg/kg of SR 4233 as an intravenous bolus in 0.5 mL Ringers solution through the dosing cannula. Dialysis sampling was continued for at least 1.5 hours after the SR 4233 was administered to the rats.

G. On-Line Interface Operation

The interface 66 between the microdialysis sampling system and the CE analysis system must perform a variety of functions. It must convert the continuous sampling stream of the microdialysis system into discrete samples for CE analysis. The interface 66 must also convert the microliter volumes of the microdialysis sample to nanoliter volumes for CE. Finally, the interface 66 must shield the experimental animal from the high voltages of the CE system. The on-line interfaces 66, 130 described in this application perform all three functions.

As shown in FIG. 6, the analyte flows directly from the experimental animal 18 into the sample loop (e.g., 236) of the microinjection valve 220. This flow is controlled by microinfusion pump 12. The microdialysis flow rate of 1 μL/minute is converted into a 60 nL plug by the sample loop within the microinjection valve. This sample plug is injected into the inlet capillary 50 line at timed intervals. The sample plug (e.g., 260) is transported to the injection interface 54 by the flow of CE run buffer controlled by the transfer microinfusion pump 34. Pump 34 is continuously pumping CE run buffer through the transfer line 50 into the well within the CE interface 54. As shown in FIG. 10, the sample plug 268 exits the transfer line 50 into the CE run buffer reservoir well 148 directly across from the upstream end 192 of the outlet (CE) capillary 188. An electrical run potential is constantly applied to the CE system such that buffer is continuously being drawn into the outlet capillary 188 flow passageway 190 from the run buffer reservoir 148 by electrosmotic flow. Injection of the sample plug into the flow passageway 190 of the outlet capillary 188 is accomplished because it is captured by the outlet capillary 188 as it passes near the orifice. Any sample not captured by the CE capillary 188 is swept away from the injection region by the run buffer pumped through the transfer line behind the sample plug.

Proper operation of the injection interface requires careful positioning of the transfer (inlet) capillary 168 relative to the CE (outlet) capillary 188. The open design of this interface allows for ready control and optical determination of positioning. In addition, the run buffer reservoir well 148 can be arbitrarily large. A relatively large reservoir well 148 volume provides enhanced CE run buffer stability and system reproducibility. Fresh CE run buffer is continually being pumped into the well 148 through the sample transfer line 168 at a rate of 5 μL/minute. With a 90 second interval between injections, 60 nL of sample is followed by 7.5 μL of buffer. Therefore the injection interface well 148 is well-flushed between injections and the composition of the CE run buffer in the reservoir does not change as samples are injected.

H. Interface Optimization

Several operational parameters were investigated in relationship to their affect on CE performance in terms of peak response and shape. These included the transfer capillary positioning, transfer flow rate, and transfer capillary inner diameter. Additionally, the operation of the microinjection valve was found to play a critical role in CE peak shape. The experimental antineoplastic SR 4233 was used as a test compound for these evaluations.

Transfer capillary positioning. The design of the injection interface (FIG. 2) using four guide tubes 88, 90, 94, 96 effectively aligns the transfer (inlet) capillary 98 with the CE (outlet) capillary 110 in two dimensions. The effect of varying the third dimension, the distance between the capillaries or interface gap, was studied at a transfer flow rate of 5 μL/minute with the results as shown in Table I.

TABLE 1

| CE Peak Parameters as a Function of Injection Gap | | | |
|---|---|---|---|
| Gap (μm) | Peak Height (afu[a]) | Peak width[b] (sec) | Peak Symmetry[c] |
| 50 | 1312 ± 23 | 2.82 ± 0.08 | 0.77 ± 0.03 |
| 100 | 1416 ± 29 | 2.86 ± 0.07 | 0.78 ± 0.03 |
| 300 | 690 ± 118 | 5.1 ± 0.63 | 0.80 ± 0.04 |

[a] arbitrary fluorescence units
[b] width at half-height
[c] peak symmetry is defined as the ratio of area before the peak to the area after the peak.

As the gap increases in distance both peak height and peak shape deteriorate. Operation of this injection interface 66 requires efficient transfer of the sample plug across the interface gap into the region 112 being sampled electrosmotically by the CE. From the data of Table I this transfer is efficient with gaps less than 100 μm. At larger gap distances, the sample plug disperses into the run buffer reservoir 80 and is sampled less efficiently resulting in smaller CE peak heights. The CE peak is also much broader as the dispersed sample is less efficiently swept away from the interface by the following transfer buffer. An interface gap distance of 50 μm was used for all subsequent experiments. This distance is easily achieved and provides good operation. Smaller gap distances can provide marginally better operation but require more care in fabrication.

Transfer buffer flow rare. The second parameter investigated was the flow rate of the transfer buffer. The transfer buffer flow has two effects at the injection interface. The first effect is the transport of the sample plug into the CE electrosmotic injection region. The second effect is the removal of uninjected sample from the injection region. As seen from the dam in Table II, CE peak height decreases while peak shape improves as the transfer flow rate increases.

TABLE II

| CE Peak Parameters as a Function of Transfer Flow Rate | | | |
|---|---|---|---|
| Flow Rate (ul/min) | Peak Height (afu[a]) | Peak Width[b] (sec) | Peak Symmetry[c] |
| 1.0 | 2532 ± 186 | 10.27 ± 0.82 | 0.76 ± 0.02 |
| 3.0 | 1826 ± 278 | 4.36 ± 0.57 | 0.77 ± 0.03 |
| 5.0 | 1437 ± 134 | 2.82 ± 0.10 | 0.76 ± 0.02 |
| 10.0 | 1075 ± 60 | 2.06 ± 0.06 | 0.75 ± 0.03 |

[a] arbitrary fluorescence units
[b] width at half-height
[c] symmetry is defined as the ratio of area before the peak to the area after the peak.

Using a 50 μm interface gap, transfer from the transfer capillary 98 into the outlet capillary 110 zone appears to be extremely efficient even at the lowest transfer flow rates. In this case, the residence time of the sample plug in the flow path 112 determines the peak height rather than dispersion of the sample. The residence time of the sample plug also determines the CE peak shape. As the residence time increases the peak width increases as a larger sample volume is injected into the outlet capillary 110. A faster transfer flow more efficiently sweeps the sample plug past the inlet to the outlet capillary 110. A compromise must therefore be made between CE peak height and peak shape. A transfer flow rate of 5 microliterL/minute results in a decrease in CE peak height of less than 50% relative to a 1 microliterL/minute transfer flow rate but an improvement in peak width of over three fold. Faster transfer flow rates result in only marginal improvements in peak shape but large decreases in peak height. A transfer flow rate of 5 microlitersL/minute was used in all subsequent experiments.

Transfer capillary inner diameter. Transfer capillaries of 25 μm and 50 μm were evaluated. The general performance of the interface was the same for both diameters except that the smaller diameter capillaries are less sensitive to the interface gap distance. The 50 μm capillary showed decreased performance at 300 μm while the 25 μm capillary showed no decrease at this gap distance. However, the 25 μm transfer capillary was more prone to clogging during the extended operation required of this system. Pharmacokinetic experiments of the type for which this invention is well suited may last for several hours during which time the system remains in continuous use. Any extended operational difficulty will likely result in the loss of the entire experiment. Therefore, system reliability is of extreme importance. Transfer capillaries with inner diameters of 50 μm were chosen for optimal performance and reliability. Larger capillaries require smaller transfer gap distance with only marginal improvements in reliability while 25 μm capillaries provide little improvement in performance but are considerably less reliable.

Microinjection valve operation. In studying the CE peak shape during the interface optimization, it was noted that all of the CE peaks exhibited considerable tailing. Optimization of the interface parameters improved the CE peak widths at half-height but did not decrease the tailing. It was ultimately determined that the peak tailing resulted from dead volumes associated with the microinjection valve. With a sample loop of only 60 nL, the exit port (transfer tube 256) contributes a significant volume to the system. The commercial valve 220 (FIG. 6) used in these experiments had an exit port 256 diameter of 0.010 inch which results in a port volume of about 90 nL. This dead volume results in the tailing observed in initial experiments. To minimize the peak tailing, the operation of the microinjection valve 220 was modified. Initially, the valve was allowed to remain in the inject position for a relatively long time (i.e. 15 seconds). By decreasing the time the valve is in the inject position the effect of the exit port dead volume can be minimized. Decreasing the injection time dramatically decreases the peak tailing with no effect on peak height until injection time is less than 3 seconds. A peak clippings' time of 3 seconds was used in all subsequent experiments. It should be noted that specially drilled microinjection valves are now available which may eliminate much of the dead volume encountered with the current valve.

Comparison to off-line injection. The optimized on-line system was compared to off-line electrokinetic injection. Off-line injections of 1 to 5 seconds at 25 kV were made. Comparing the peak height of samples using on-line injection to off-line injection showed a dilution factor of 4 for on-line injection. Comparison was made to off-line injections of 2 second duration as these gave similar efficiencies to on-line injections.

I. System Response

Because this system is designed to study transient signals in vivo, the response time of the system is a critical parameter. The response of the system to a concentration change was first examined by flow injection directly from the dialysis pump 12 (FIG. 1) into the microinjection valve 22. This was accomplished by replacing the microdialysis probe 16 with a switching valve (now shown). The pump 12 used in the experiments was one that can control three dispensing syringes (not shown) simultaneously. Therefore, it was possible to instantaneously switch between solutions of two different concentrations of SR 4233 and a blank solution. This allowed the determination of the response time of the interface 54 alone without contributions from microdialysis sampling. With injections being made every 90 seconds, the response to an input concentration change is essentially instantaneous. This result was to be expected because at the dialysis flow rate of microliterL/minute, the 60 nL sample loop is filled in less than four seconds. The peak height precision was 2.6% RSD.

The response time was then investigated in the complete microdialysis sampling mode. In this case the microdialysis probe was used to sample a test solution. Three small beakers containing solutions of two different concentrations of SR 4233 and a blank were used. To create the concentration steps the microdialysis probe 16 was rapidly switched from one beaker to another (not shown). Again an instantaneous response was obtained on the time scale of the CE step. The small peaks found after stepping back to the blank solution are an artifact of the manual switching of the microdialysis probe 16 between beakers. The peak height precision was again found to be 2.6% RSD indicating that the microdialysis sampling did not significantly affect system performance.

J. Determination of SR 4233 Pharmacokinetics

To evaluate the performance of this system for an actual pharmacokinetic experiment, the antineoplastic SR 4233 was investigated in the rat. Typical electropherograms of blood dialysates both before and after dosing with SR 4233 were obtained using on-line microdialysis sampling/CE detection system described above. SR 4233 can be resolved from its main metabolite SR 4317 in 60 seconds. No interferences are observed in the blank. Using this separation, microdialysis sampling could be continuously accomplished on-line with a 90 second sampling interval. In addition to the usual elimination phase, the rapid distribution phase is also observable. From a non-linear least squares fit of the data the half-life of elimination was determined to be 15.3±1.0 minutes and the half-life of distribution was determined to be 1.1±0.2 minutes (n=3 in both cases). It is only because of the rapid sampling and analysis capabilities of this system that the distribution kinetics could be determined.

CONCLUSIONS

Microdialysis sampling provides a powerful tool for monitoring biochemical reactions in vivo. The temporal resolution of the microdialysis experiment has been limited by the sample volume requirement and/or detection limit of the associated analysis technique. Refinement of the microdialysis experiment can be realized by moving the analysis step on-line to eliminate any sample manipulation. However, this limits the temporal resolution of the experiment to the speed of the analysis step. The work described in this application demonstrates the high temporal resolution that can be achieved using on-line capillary electrophoresis for the analysis of microdialysis samples due to the low sample volume requirement and high separation speed.

The on-line coupling of CE to microdialysis sampling offers other advantages as well. The high ionic strength of the dialysate, necessary for biocompatibility, is well tolerated by the CE system in contrast to alternative on-line techniques such as mass spectrometry. CE also offers an alternative separation mode to LC. Many biologically important compounds are charged and therefore ideally suited to an electrophoretic separation.

This system provides the capability of near real-time determination of multiple species in a conscious, freely-moving animal. In essence, the on-line microdialysis/CE system represents a separation based biosensor with multiple analyte capabilities. The delay between the event occurring in the animal and the output of the analytical data is on the order of 5 minutes. Indeed most of this delay is the time needed to move the sample from the animal to the microinjection valve. This delay can be greatly reduced using anesthetized or restrained animals, by positioning the microinjection valve closer to the implanted microdialysis probe. It should be noted that this delay does not represent a "time constant" for the system but a true delay as proper construction of the flow system results in minimal band broadening.

The speed of separation used for this work does not approach the limit that can be achieved by CE. It was chosen primarily to assess the operation of the interface at a pharmacokinetically useful sampling rate which could be readily achieved. As the separation speed improves to less than 30 seconds, the fundamental limitation of the microdialysis membrane response time and therefore the lower limit of temporal resolution for microdialysis sampling may be approached. The near real-time monitoring abilities of this system may prove useful in fundamental experiments by allowing feedback of information for experimental manipulation. An even more powerful use of such a system could lie in critical care monitoring of patients where rapid turnaround of analysis results is essential.

What is claimed is:

1. An interface unit for use in the fluid flow oath between a sequential, multiple, in vivo sample acquisition device and capillary electrophoresis detection device, the interface unit comprising
   (1) a body member having a base and an upstanding wall defining a generally hollow interior well, the upstanding wall including an inlet passageway and an outlet passageway,
   (2) an inlet guide member having an axially extending guide passageway disposed coaxially within the inlet passageway,
   (3) an outlet guide member having an axially extending guide passageway disposed coaxially within the outlet passageway,
   (4) an inlet capillary tube means having an outer diameter sized for being received by the axially extending passageway of the inlet guide member, and a fluid passageway through which analyte can flow, a first end disposed exteriorly of the well in fluid communication with the sample acquisition device and a second end disposed within the well,
   (5) an outlet capillary tube means having an outer diameter sized for being received in the axially extending guide passageway of the outlet guide member, and a fluid passageway through which analyte can flow, a first end disposed within the well, and a second end disposed exteriorly of the well in fluid communication with the capillary electrophoresis device, and
   (6) means for electrically isolating the interface unit from the sample acquisition device.

2. The device of claim 1 wherein the second end of the inlet capillary tube means and the first end of the outlet capillary tube means are disposed in an opposed, adjacent but separated relation to foster the electrokinetic flow of a portion of the analyte from the inlet capillary tube means into the fluid passageway of the outlet capillary tube means.

3. The device of claim 1 wherein the inlet guide member extends through the inlet passageway, and includes adhesive means for fixedly coupling the inlet guide member to the wall, and the outlet guide member extends through the outlet passageway and includes adhesive means for fixedly coupling the guide member to the wall.

4. The device of claim 1 wherein the body member is composed of a generally non-conductive material, and the well is large enough to hold between about 1 and 6 ml. of fluid along with a grounding electrode from the capillary electrophoresis device.

5. The device of claim 4 wherein the upstanding wall terminates at a lip to define a top opening of the well and wherein the body means includes a cap means for sealingly engaging the lip means to enclose the well.

6. The device of claim 4 wherein the inlet capillary tube means and the outlet capillary tube means are disposed generally coaxially.

7. The device of claim 6 wherein the second end of the inlet capillary tube means, and the first end of the outlet capillary tube means are disposed in an opposed relation, and spaced less than about 300 micrometers from each other.

8. The device of claim 7 wherein the inlet capillary tube means has an inner diameter of between about 20 and 100 micrometers and is sized to accommodate flow rates of between about 0.5 and 10.0 microliters per minute of analyte.

9. The device of claim 1 wherein the upstanding wall includes a radially inner surface and a radially outer surface, and the inlet passageway includes an enlarged portion adjacent to at least one of the radially inner surface and the radially outer surface, the enlarged portion being sized and positioned for receiving an adhesive means for fixedly attaching the inlet guide member to the inlet passageway.

10. The device of claim 1 wherein the outlet passageway includes an enlarged portion adjacent to at least one of the radially inner surface and radially outer surface of the upstanding wall, the enlarged portion being sized and positioned for receiving an adhesive means for fixedly attaching the outlet guide member to the outlet passageway.

11. The interface of claim 1 wherein the base includes a top surface that defines the bottom of the well, and the inlet and outlet capillary tube means are positioned in a spaced relation from the bottom of the well at a distance sufficient to permit the placement of a stirring rod means below the inlet and outlet capillary tube means.

12. A valve and interface system for use in the fluid flow path between a generally continuous sample acquisition device and a capillary electrophoresis detection device, the valve comprising
   (1) a collection port for receiving a continuous flow of analyte from the sample acquisition device couple to an analyte source,
   (2) a dispensing port for dispensing analyte from the valve to the interface unit, and (3) a transfer container means for transferring a discrete analyte plug from the collection port to the dispensing port, and (4) a flushing agent receiving means for directing a stream of flushing agent to the dispensing port, and the interface unit comprising (5) a body member having a base and an upstanding wall defining a generally hollow interior well, the upstanding wall having an inlet passageway and an outlet passageway, (6) an inlet capillary tube means having a fluid passageway through which analyte can flow, a first end disposed exteriorly of the well, and a second end disposed with the well, and (7) an outlet capillary tube means having a fluid passageway through which analyte or buffer can flow to the capillary electrophoresis device, a first end disposed within the well, and a second end disposed exteriorly of the well, and wherein the system further includes means for electrically isolating the sample acquisition device from the capillary electrophoresis device.

13. The device of claim 12 wherein the second end of the inlet capillary tube means, and the first end of the outlet capillary tube means are disposed in an opposed, adjacent, but separated relation to foster the flow of a portion of the analyte from the inlet capillary tube means into the fluid passageway of the outlet capillary tube means.

14. The device of claim 12 wherein the inlet capillary tube means and outlet capillary tube means are disposed generally coaxially, and the second end of the inlet capillary tube means and the first end of the outlet capillary tube means are spaced less than about 300 micrometers from each other.

15. The device of claim 12, wherein the interface unit includes (1) an inlet guide member having an axially extending guide passageway disposed coaxially with the inlet passageway, and sized to receive the inlet capillary tube means, and (2) an outlet guide member having an axially extending guide passageway disposed coaxially with the outlet passageway, and sized for receiving the outlet capillary tube means.

16. The device of claim 15 wherein (1) the inlet guide member extends through the inlet passageway and includes adhesive means for fixedly coupling the inlet guide member to the wall, and (2) the outlet guide member extends through the outlet passageway and includes adhesive means for fixedly coupling the outlet guide member to the wall.

17. The device of claim 12 wherein the inlet capillary tube means is sized to accommodate flow rates of between about 0.5 and 10.0 microliters per minute of analyte.

18. The device of claim 12 wherein the collection port includes an analyte receiving means disposed upstream from the transfer container, and an analyte discarding means disposed downstream from the transfer container, whereby during operation of the device, analyte is generally continuously flowing from the analyte receiving means, through the transfer container, and out the analyte discarding means, and the collection port is maintained in electrical isolation from the dispensing port.

19. The invention of claim 12 wherein the transfer container includes a first transfer container and a second transfer container, the first and the second transfer containers being movable between the collection port and the dispensing port, whereby, when the first transfer container is positioned at the collection port to receive analyte, the second transfer container is positioned at the dispensing port to dispense at least one of the analyte plug and flushing agent.

20. The device of claim 19, further comprising a transfer tube means for transferring analyte and flushing agent from the valve to the interface, whereby when first transfer container is positioned at dispensing port, to dispense at least one of the analyte plug and flushing agent to the transfer tube means, the second transfer container is positioned at the collection port to receive analyte from the analyte receiving means.

21. The device of claim 20 wherein each of the first and second transfer containers comprises at least two transfer containers, and wherein the transfer tube means comprises the inlet capillary tube means.

22. The device of claim 12 wherein the generally continuous sample acquisition device comprises a microdialysis device implanted in a live animal.

23. The device of claim 12 wherein the generally continuous sample acquisition device comprise an ultrafiltration device implanted in a live animal.

* * * * *